United States Patent [19]
Rudko et al.

[11] Patent Number: 5,125,926
[45] Date of Patent: Jun. 30, 1992

[54] HEART-SYNCHRONIZED PULSED LASER SYSTEM

[75] Inventors: Robert I. Rudko, Holliston; Stephen J. Linhares, Taunton, both of Mass.

[73] Assignee: Laser Engineering, Inc., Milford, Mass.

[21] Appl. No.: 586,951

[22] Filed: Sep. 24, 1990

[51] Int. Cl.$^5$ .................................. A61N 5/06
[52] U.S. Cl. ........................ 606/19; 606/12; 606/14
[58] Field of Search .............. 128/395, 397, 398; 606/7, 10-19

[56] References Cited
U.S. PATENT DOCUMENTS 4,658,817 4/1987 Hardy .................... 606/19
4,788,975 12/1988 Shturman .................... 606/7

Primary Examiner—David M. Shay
Attorney, Agent, or Firm—Iandiorio & Dingman

[57] ABSTRACT

A heart-synchronized pulsed laser system includes a laser; a device for sensing the contraction and expansion of a beating heart to be synchronized with the laser; a device, responsive to the device for sensing, for generating a trigger pulse; a control for positioning the leading edge of the trigger pulse during the contraction and expansion cycle of the heartbeat; a control for defining the width of the trigger pulse to occur during the heartbeat cycle; and a circuit responsive to the trigger pulse for firing the laser to strike the beating heart at the time indicated by the trigger pulse position and for the period indicated by the width of the trigger pulse.

17 Claims, 4 Drawing Sheets 5,125,926

HEART-SYNCHRONIZED PULSED LASER SYSTEM

FIELD OF INVENTION

This invention relates to a heart-synchronized pulsed laser system, and more particularly to such a system which operates on a beating heart between the R and T waves of the electrocardiogram (ECG) signal.

RELATED CASES

This application is related to and incorporates herein by reference the following applications having common inventors and assignee and filed on even date herewith:

"Long Pulse, Fast Flow Laser System and Method", by Robert I. Rudko U.S. patent application Ser. No. 07/586,885;

"Handpiece for Transmyocardial Vascularization Heart-Synchronized Pulsed Laser System", by Robert I. Rudko U.S. patent application Ser. No. 07/586,891; and "Heart-Synchronized Vacuum-Assisted Pulsed Laser System and Method", by Robert I. Rudko U.S. patent application Ser. No. 07/586,884.

BACKGROUND OF INVENTION

The heart muscle receives its blood supply from the coronary artery, which feeds out and around into the outside of the heart muscle. Some time ago it was noticed that reptilian hearts had no arterial supply to the heart muscle. Rather, the reptilian heart blood supply was delivered through the inside wall of the heart directly to the heart muscle. The thought occurred that this could be an alternative to the heart bypass technique which can usually be applied to a patient no more than twice: after two bypass operations the risks outweigh the benefits and the patient is generally without further recourse. In an attempt to imitate the reptilian condition, tiny holes were made in mammalian hearts with hot wires or needles but this met with limited success. Although the holes healed from the outside and did allow for some internal blood delivery, the holes soon healed over entirely and cut off the blood supply. The protocol was then developed using a laser to make the holes and this met with much greater success. This technique is known as transmyocardial revascularization (TMR).

However, the laser technique introduced a host of new problems. The heart is extremely sensitive to a laser pulse at certain times during its cycle. A laser pulse striking the heart at the T time of the ECG wave, for example, could cause the heart to fibrillate and result in heart failure. If the heart is stopped during the procedure this problem can be avoided. But stopping the heart requires cooling the heart and connecting the patient to a heart-lung machine with all the attendant increased risks that this brings including prolonged recovery times. A beating heart, on the other hand, is difficult to administer this technique to because as the heart contracts and expands the surface may not remain normal to the laser beam, the heart wall changes distance from the focus of the beam, and the thickness of the wall changes so that the positioning of the laser handpiece and the power of the beam required are varying and unpredictable. This makes precise location of laser beam on the heart difficult so that not only will the holes not be properly located, but other areas of the heart which should not be struck may well be struck. Further, when the technique requires stopping the heart the chest must be cut open including cutting the sternum, which is especially risky because the sternum is a primary source of red blood cells.

SUMMARY OF INVENTION

It is therefore an object of this invention to provide a laser system for performing transmyocardial revascularization on a beating heart.

It is a further object of this invention to provide such a laser system which is synchronized to operate at a specific time in the heart's beating cycle when accuracy is enhanced and risks are reduced.

It is a further object of this invention to provide such a laser system which is synchronized to operate between the R and T waves of the heart's ECG.

It is a further object of this invention to provide such a laser system which provides shorter pulses that interfere less with the heart function and make cleaner holes.

It is a further object of this invention to provide such a laser system which times the laser pulses to occur when the heart surface is relatively stable to enhance the accuracy of laser aiming and focusing and minimize the risk of striking an undesirable part of the heart.

It is a further object of this invention to provide such a laser system which times the laser pulses to occur when the heart wall is at a point in its cycle when it is electrically least sensitive to interference with its functioning.

It is a further object of this invention to provide such a laser system which substantially reduces the chance of inducing fibrillation.

It is a further object of this invention which provides such a laser system which is safe, requires no attachment of the patient to a heart-lung machine, no cooling of the heart, and no opening of the sternum.

It is a further object of this invention to provide such a laser system which requires only a simple incision between the patient's ribs and results in less trauma, faster recovery and less blood loss.

The invention results from the realization that a pulsed laser system can be achieved for operating on a beating heart accurately, with minimal interference to the heart and minimal risk to the patient by synchronizing the pulsing of the laser to the ECG of the heart so that laser pulses can be administered to the heart only during the moment when the heart is most still, least sensitive electrically, during the period between the R and the T waves of the ECG.

This invention features a heart-synchronized pulsed laser system including a laser system. There are means for sensing the contraction and expansion of a beating heart which is to be synchronized with the laser. There are means, responsive to the means for sensing, for generating a trigger pulse in response to the ECG signal, as well as means for positioning the leading edge of the trigger pulse during the contraction and expansion cycle of the heartbeat, and means for defining the width of a trigger pulse to occur during the heartbeat cycle. There are means responsive to the trigger pulse for firing the laser to strike the beating heart at the selected time indicated by the trigger pulse position and for the period indicated by the width of the trigger pulse.

In a preferred embodiment, the means for sensing the contraction and expansion includes means for sensing the ECG signal of the beating heart. There is a laser delivery system which may include an articulated beam delivery arm or a fiber optic element. The means for sensing the ECG signal of the beating heart may be an ECG unit and the means for generating the trigger pulse may do so in response to the R wave of the ECG. In the means for positioning, the leading edge of the trigger pulse may position the trigger pulse between the R and the T waves of the ECG. The means for defining the pulse width of the trigger pulse may define a pulse width which occurs in the period between the R and the T waves of the ECG.

The means for generating may include a marker pulse circuit for generating a specific time in a heartbeat cycle of the ECG for providing a marker pulse representative of that time. The means for generating may further include a trigger pulse circuit responsive to the marker pulse circuit for providing a trigger pulse whose position in the heartbeat cycle is a function of the specific time in the cycle represented by the marker pulse. The trigger pulse circuit may include means for delaying the marker pulse to locate it at a selected position relative to its initial position in the heartbeat cycle, and means for adjusting the duration of the marker pulse to a selected time to create the trigger pulse of the selected position and width.

The means for firing may include gate means for inhibiting delivery of the trigger pulse to the laser and may further include switch means for enabling the gate means to deliver the trigger pulse to the laser. There may be an arming circuit for further inhibiting delivery of the trigger pulse to the laser, and arming switch means for enabling the arming circuit to deliver the trigger pulse to the laser.

DISCLOSURE OF PREFERRED EMBODIMENT

Other objects, features and advantages will occur to those skilled in the art from the following description of a preferred embodiment and the accompanying drawings, in which.

Figure 1:
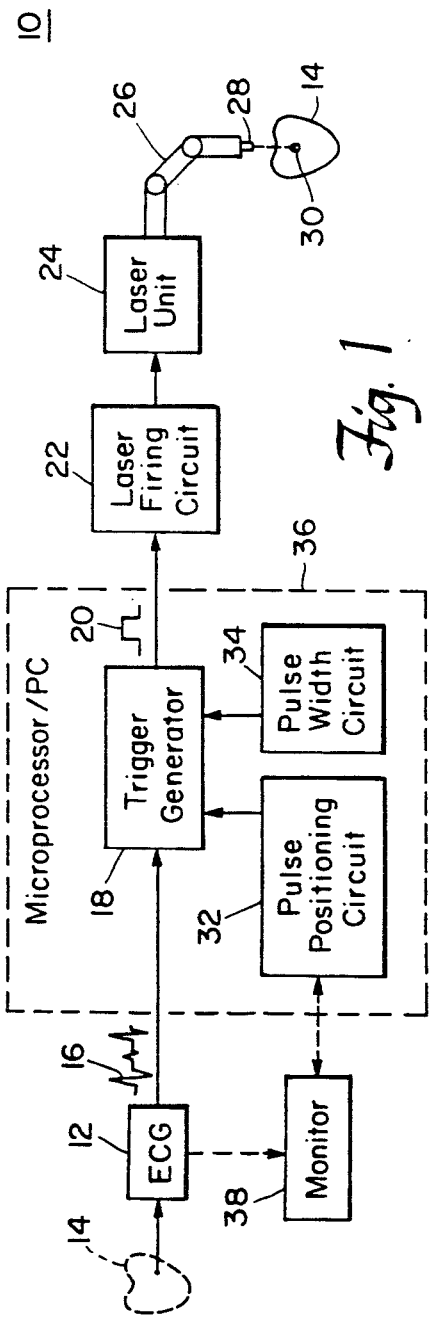
FIG. 1 is a schematic block diagram of a heart-synchronized pulsed laser system according to this invention.

This invention may be accomplished in a heart-synchronized pulsed laser system having a laser and a laser beam delivery system. The laser is typically a pulsed 50 Joules $CO_2$ laser. The laser beam delivery system may be an articulated optical arm or a fiber optic element with a suitable handpiece or terminal optics at the distal end for delivering the laser beam for perforating the heart. There is some means for sensing the electrocardiogram signal of the beating heart to be synchronized with the laser. This may be a standard ECG device such as obtainable from Hewlett-Packard Company. The system uses some means for generating a trigger pulse in response to the ECG signal. Typically the trigger pulse is a function of the R wave of the heartbeat cycle generated by the conventional ECG equipment. The heartbeat cycle has four distinct waveforms, the Q, the R, the S, and the T. There are means for setting the beginning of the trigger pulse so that it occurs in the proper time relationship to the R wave and ends before the T wave to avoid interference with the electrical characteristics of the beating heart. The pulse positioning circuit locates the leading edge of the trigger pulse and a pulse width circuit determines the width so that it extends over only the necessary and safe duration of the heartbeat cycle. The trigger pulse is passed to a laser firing circuit, which then operates the laser to produce a pulsed laser beam to the delivery system which the surgeon aims precisely at the beating heart preferably during the time between the R and T waves of the heartbeat cycle where the heart is most static, and the accuracy is most assured.

The trigger generator may include a marker pulse circuit for detecting a specific time in the heartbeat cycle of the ECG signal and providing a marker pulse representative of that time. The time may be when the R wave crosses a particular threshold or some time related to that time. The marker pulse circuit may be built in as a part of the readily obtainable ECG unit such as a type HP78352A obtainable from Hewlett-Packard Company. The trigger pulse circuit, also is the means for generating the trigger pulse, responds to the marker pulse circuit to provide a trigger pulse whose position in the heartbeat cycle is a function of that specific time in the cycle represented by the marker pulse. The trigger pulse circuit typically includes means for delaying the marker pulse to locate it at a selected position relative to its initial position in the heartbeat cycle, and also contains means for adjusting the delay of the marker pulse to a selected time to create the trigger pulse of the selected position and width. The position of the trigger pulse and its width may be adjusted by a pulse positioning circuit and a pulse width circuit. The laser firing circuit includes a gate which inhibits delivery of the trigger pulse to the laser unless a foot switch is enabled by the surgeon when he is ready to make a hole in the heart. There is also an arming circuit which further inhibits delivery of the trigger pulse to the laser, even if the surgeon steps on the foot switch unless that arming switch has been actuated. If the arming switch is actuated and the foot switch is depressed, the next trigger pulse will be directed to fire the laser and provide a pulsed laser beam.

There is shown in FIG. 1 a heart-synchronized pulsed laser system 10 with electrocardiogram unit 12 connected to a heart 14 which is to undergo the surgery. The ECG signal 16 is delivered to trigger generator 18, which provides a trigger pulse 20 to laser firing circuit 22, which in turn energizes laser unit 24 including a laser power supply and a laser to produce a pulsed laser beam through articulated optical arm 26 into optical handpiece 28 to make a hole 30 in heart 14. The position of trigger pulse 20 in the heartbeat cycle of ECG signal 16 is determined by pulse positioning circuit 32. The width of the pulse 20 and its duration during the heartbeat cycle is determined by pulse width circuit 34. Trigger generator 18 as well as pulse positioning circuit 32 and pulse width circuit 34, may be included as an additional board in a PC or a microprocessor 36, in which case the system can be controlled through the computer keyboard and suitable software. PC 36 and ECG 12 may have separate monitors, or they may have a single monitor 38 which displays both the ECG and information about the trigger pulse 20. Trigger generator 18 may include a marker pulse circuit 50 which provides marker pulse 52 and trigger pulse circuit 54 which responds to marker pulse 52 to create trigger pulse 20. Alternatively, marker pulse circuit 50 is included in the ECG itself in some cases.

Figure 3:
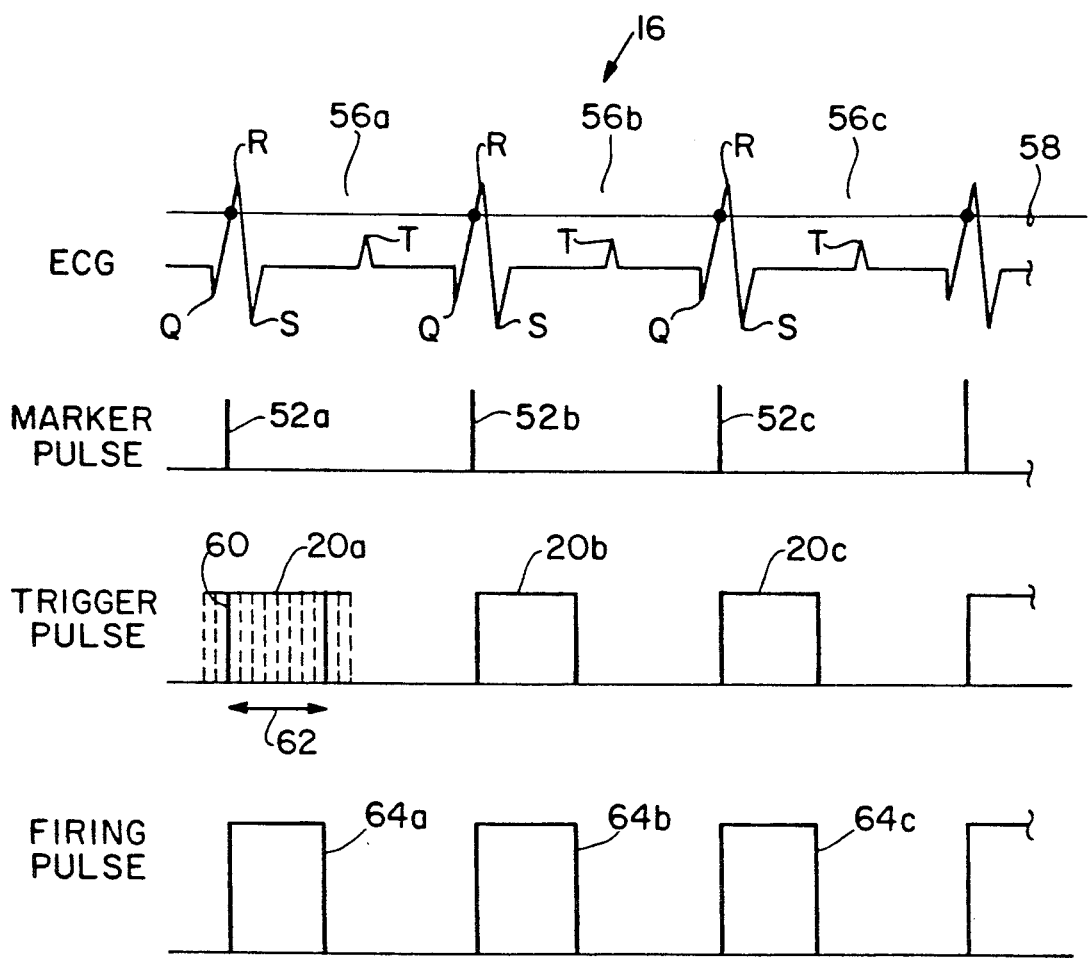
FIG. 3 illustrates the ECG signal, marker pulse, trigger pulse and firing pulse waveforms occurring in the heart-synchronized pulsed laser system described in FIGS. 1 and 2.

This can be better understood with reference to FIG. 3, where ECG signal 16 may be seen as consisting of a series of heartbeat cycles 56a, 56b, 56c each of which contains the waveforms Q, R, S and T. Where waveform R crosses preselected threshold 58, marker pulses 52a, 52b, 52c are created. Trigger pulses 20a, 20b, 20c are then created by trigger pulse circuit 54. The position of the leading edge 60 and the overall width 62 of each trigger pulse 20 is determined, respectively, by pulse positioning circuit 32 and pulse width circuit 34. In response to trigger pulse 20, a firing pulse 64 indicated as 64a, 64b and 64c, FIG. 3, is created to energize laser 24.

Figure 2:
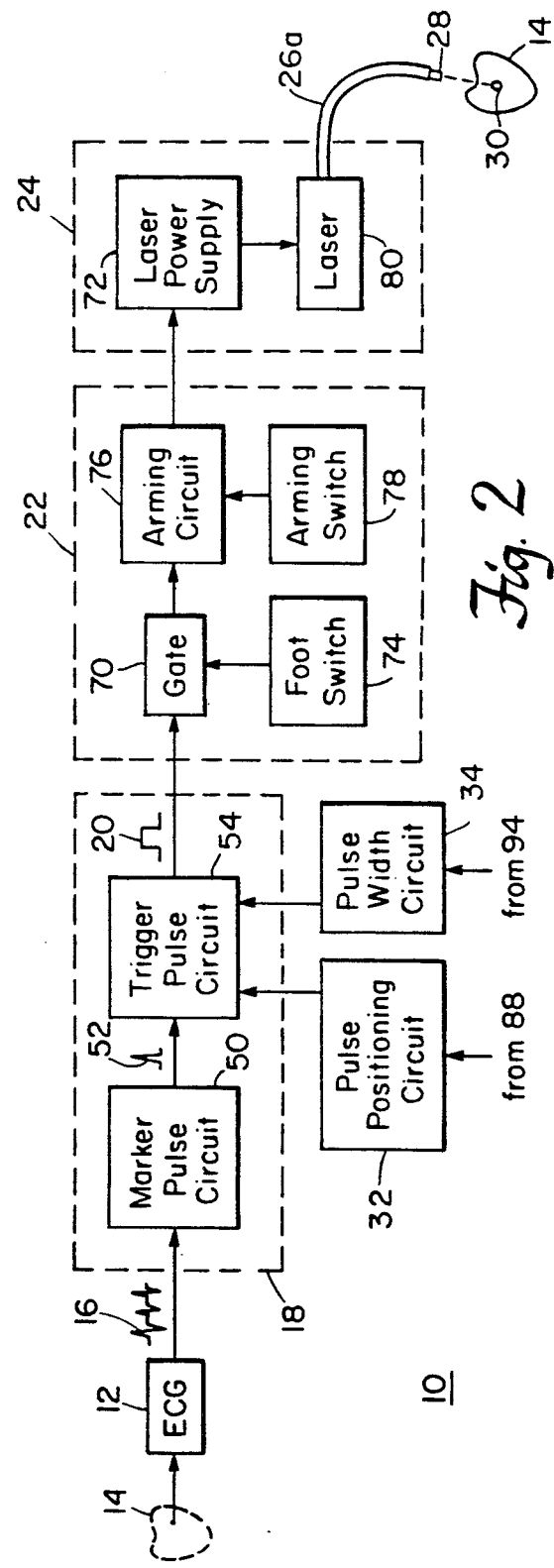
FIG. 2 is a more detailed diagram of the system of FIG. 1.

In FIG. 2, laser firing circuit 22 is shown to include gate 70 which generally inhibits the delivery of trigger pulse 20 to laser power supply 72 in laser unit 24. The inhibiting effect of gate 70 can be overcome when the surgeon steps on foot switch 74. Trigger pulse 20 is still inhibited, however, by arming circuit 76 which in turn can have its inhibiting effect overcome by the operation of arming switch 78. This double lock on the delivery of trigger pulse 20 to laser power supply 72 ensures that the firing of the laser is truly desired and not accidental. Thus the surgeon must first arm the system by operating arming switch 78 to enable arming circuit 76. Then and only then is he able to pass the next occurring trigger pulse 20 through gate 70 to the laser power supply 72 by actuating his foot switch 74. Also included in laser unit 24 is a standard $CO_2$ laser 80. The output of laser 80 may be delivered through a fiber optic element 26a to handpiece 28.

Figure 4:
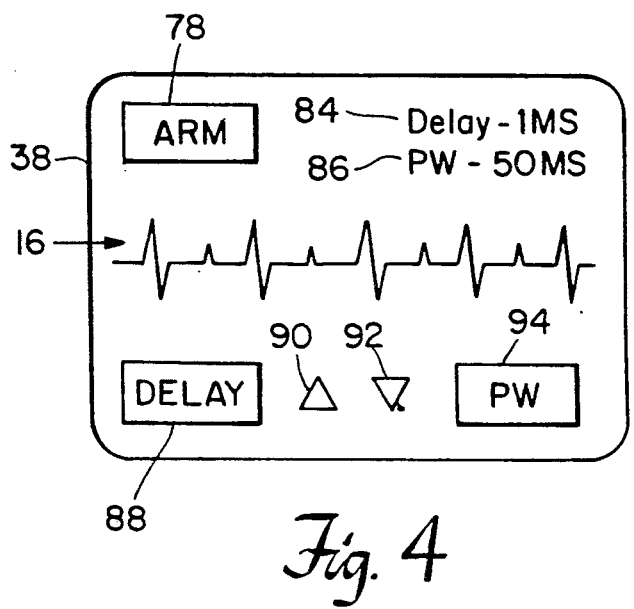
FIG. 4 is an illustration of a touch-sensitive monitor that may be used in conjunction with the system of FIGS. 1 and 2.

Monitor 38, FIG. 4, may display both the ECG signal 16 and the display of the delay 84 which has been introduced by pulse positioning circuit 32, FIG. 2, which delay is indicated as one millisecond in FIG. 4. It may also include the pulse width 86 shown as 50 milliseconds selected by the pulse width circuit 34, FIG. 2. Monitor 38 may also include a delay selection switch 88 which when pressed enables one to increase or decrease the delay time by simply touching the up 90 or down 92 arrows on the screen. Pulse width touch switch 94 may be used in the same fashion to adjust the pulse width duration.

Figure 5A:
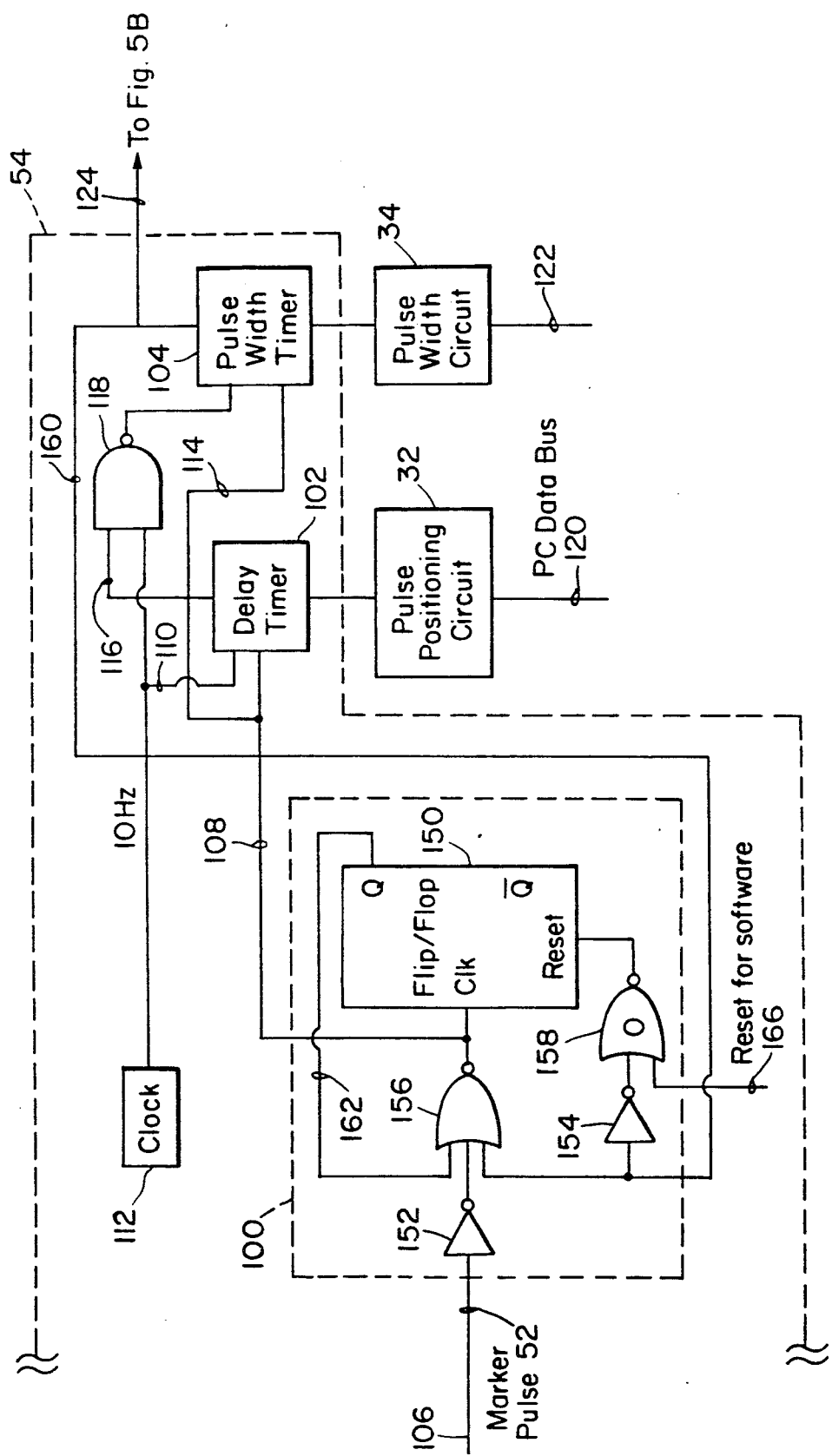
FIG. 5A is a more detailed schematic diagram of the trigger pulse circuit, pulse positioning circuit and pulse width circuit of FIG. 2.

Trigger pulse width circuit 54, FIG. 5A, may include an anti-false trigger pulse circuit 100 which prevents a false firing or second firing of the system when a firing sequence is already in progress. Also included in trigger pulse circuit 54 is a delay timer 102 and a pulse width timer 104. When marker pulse 52 on line 106 is permitted to pass through anti-false trigger pulse circuit 100, the marker pulse is input on line 108 to delay timer 102. The conjunction of the marker pulse with the input on line 110 from 10 KHz clock 112 causes delay timer 102 to set the position of the leading edge of the trigger pulse. The appearance of the marker pulse on line 108 also is delivered as an enable signal on line 114 to preset pulse width timer 104. When the leading edge position of the trigger pulse has been set by delay timer 102 a signal is provided on line 116 to NAND gate 118, which in conjunction with a signal from clock 112 causes the trigger pulse to be expanded to a predetermined width in pulse width timer 104. The specific positioning of the leading edge of the trigger pulse by delay timer 102 is controlled by pulse positioning circuit 32 which is typically a time delay data latch under control of the computer via the data bus 120. Similarly, the duration of the pulse imparted by pulse width timer 104 is controlled by pulse width circuit 34, typically a pulse width time data latch under control of the microprocessor or PC via bus 122. The trigger pulse then is delivered over line 124 to gate 70 which may include simply an NAND gate 126.

Figure 5B:
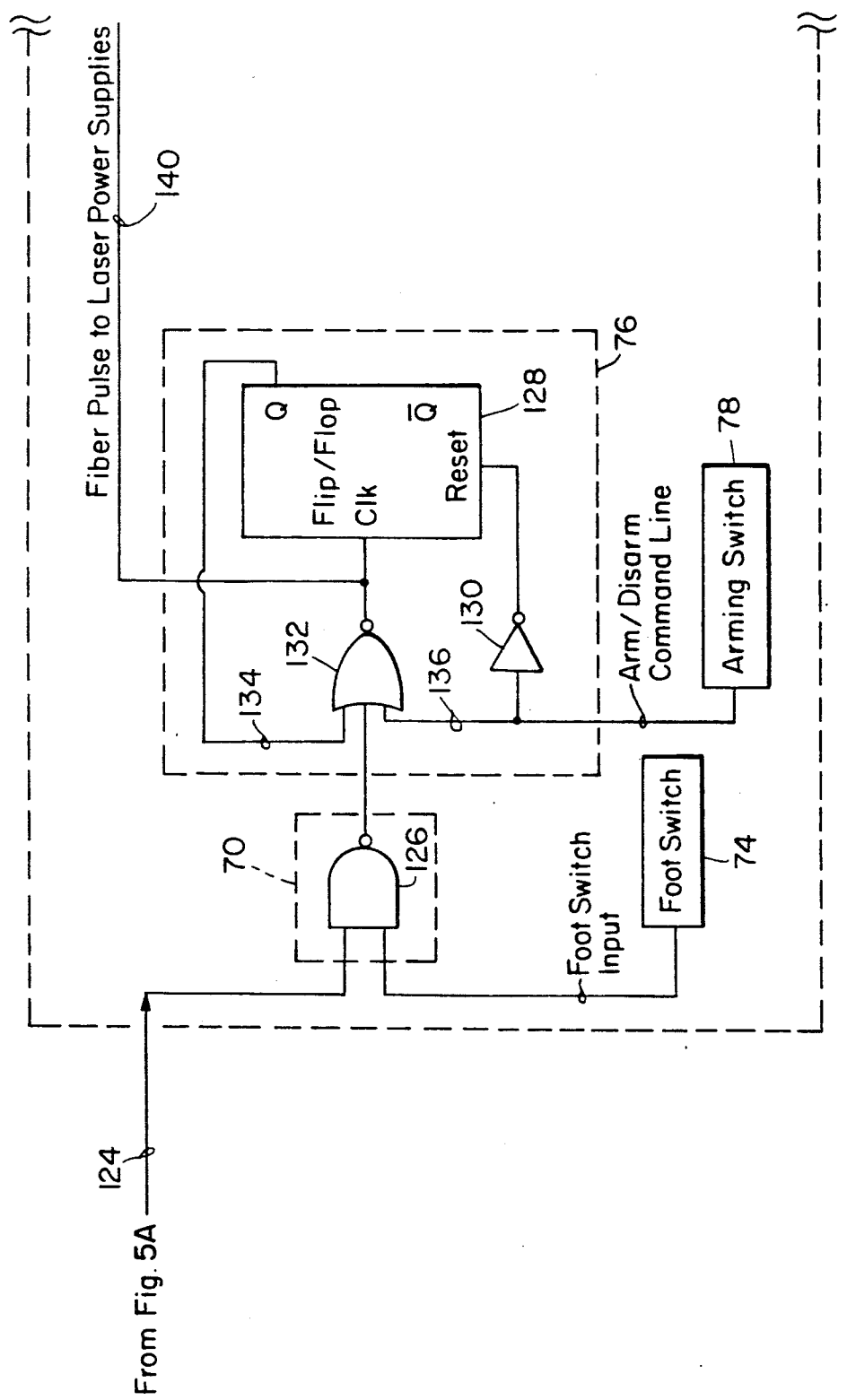
FIG. 5B is more detailed schematic diagram of the laser firing circuit of FIG. 2.

Arming circuit 76, FIG. 5B includes flip-flop 128, inverter 130, and NOR gate 132. When arming switch 78 is actuated, the signal to inverter 130 resets flip-flop 128 so that now there is a proper output on line 134 from flip-flop 128 into NOR gate 132 as well as the proper input from arming switch 78 on line 136 into NOR gate 132. Thus, when next the trigger pulse arrives on line 124, if the doctor operates the foot switch 74 the pulse will be passed through NAND gate 126 and NOR gate 132 to pass the trigger pulse on line 140 to laser power supply 72. When the trigger pulse passing through NOR gate 132 ends, the clock input to flip-flop 128 is no longer enabled and the output on line 134 ceases so that NOR gate 132 is no longer enabled to pass subsequent trigger pulses to line 140 and laser power supply 72.

The anti-false trigger pulse circuit 100 uses a flip-flop 150, two inverters 152 and 154, and two NOR gates 156 and 158. When a trigger pulse is supplied on line 124 by pulse width timer 104, it is also simultaneously placed on line 160 which is connected to inverter 154 and to NOR gate 156. At the end of the trigger pulse, the proper level appears on line 160 to enable NOR gate 156 and to reset flip-flop 150 through inverter 154 and NOR gate 158. When flip-flop 150 is reset it provides a second enabling input on line 162 to NOR gate 156. Thus when next a marker pulse 52 is delivered on line 106 and passed by inverter 152 to NOR gate 156, it is passed to line 108 and thus on to delay timer 102. The marker pulse 52 appearing on line 108 also clocks flip-flop 150 so that the proper signal is no longer on line 162 and NOR gate 156 is disabled. Until a reset occurs from the software on line 166 or the end of the trigger pulse level occurs on line 160 no further marker pulses will be passed.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A heart-synchronized pulsed laser system for performing transmyocardial revascularization on a beating heart comprising:

a laser;

means for sensing a contraction and expansion of a beating heart to be synchronized with the laser;

means, responsive to said means for sensing, for generating a trigger pulse having a width and a leading edge;

means for positioning the leading edge of said trigger pulse only at a time during the contraction and expansion cycle of the heartbeat which would not cause fibrillation of the heart;

means for defining the width of the trigger pulse to occur during the heartbeat cycle; and means, responsive to said trigger pulse, for firing said laser to strike the beating heart at the time indicated by the trigger pulse position and for a period indicated by the width of the trigger pulse.

2. The heart-synchronized pulsed laser system of claim 1 in which said laser includes a laser beam delivery system.

3. The heart-synchronized pulsed laser system of claim 2 in which said laser delivery system includes an articulated beam delivery arm.

4. The heart-synchronized pulsed laser system of claim 2 in which said laser delivery system includes a fiber-optic element.

5. The heart-synchronized pulsed laser system of claim 1 in which said means for sensing the contraction and expansion includes means for sensing an ECG signal of the beating heart.

6. The heart-synchronized pulsed laser system of claim 5 in which said means for sensing the ECG signal of the beating heart is an ECG unit.

7. The heart-synchronized pulsed laser system of claim 5 in which said means for generating generates a trigger pulse in response to an R wave of the ECG signal.

8. The heart-synchronized pulsed laser system of claim 5 in which said means for positioning sets the leading edge of said trigger pulse in the period between R and T waves of the ECG signal.

9. The heart-synchronized pulsed laser system of claim 5 in which said means for defining defines the pulse width of said trigger pulse in the period between R and T waves of the ECG signal.

10. The heart-synchronized pulsed laser system of claim 5 in which said means for generating includes a marker pulse circuit for detecting a specific time in a heartbeat cycle of the ECG signal and providing a marker pulse representative thereof.

11. The heart-synchronized pulsed laser system of claim 10 in which said means for generating further includes a trigger pulse circuit, responsive to said marker pulse circuit, for providing a trigger pulse the position of which in the heartbeat cycle is a function of said specific time in the cycle represented by said marker pulse.

12. The heart-synchronized pulsed laser system of claim 11 in which said trigger pulse circuit includes means for delaying said marker pulse to locate it at a selected position relative to said pulse's initial position in the heartbeat cycle, and means for adjusting the duration of the marker pulse to a selected time to create said trigger pulse having a positioned leading edge and a defined width.

13. The heart-synchronized pulsed laser system of claim 1 in which said means for firing includes gate means for inhibiting delivery of said trigger pulse to said laser.

14. The heart-synchronized pulsed laser system of claim 13 in which said means for firing includes switch means for enabling said gate means to deliver said trigger pulse to said laser.

15. The heart-synchronized pulsed laser system of claim 13 in which said means for firing includes an arming circuit for further inhibiting delivery of said trigger pulse to said laser.

16. The heart-synchronized pulsed laser system of claim 15 in which said means for firing includes arming switch means for enabling said arming circuit to deliver said trigger pulse to said laser.

17. A heart-synchronized pulsed laser method for performing transmyocardial revascularization on a beating heart, comprising:
generating a trigger pulse in response to an ECG signal of a beating heart to be synchronized with a laser, said trigger pulse having a width and a leading edge;
positioning the leading edge of the trigger pulse only at a time during the ECG heartbeat cycle which would not cause fibrillation of the heart;
defining the width of the trigger pulse to occur within the duration of the heartbeat cycle of the ECG signal; and
applying the trigger pulse to fire the laser and to strike the beating heart at the time indicated by the trigger pulse position and for a period indicated by the width of the trigger pulse.

* * * * *